United States Patent
Senderoff et al.

(10) Patent No.: US 8,071,090 B2
(45) Date of Patent: Dec. 6, 2011

(54) STABILIZED THROMBIN COMPOSITIONS

(75) Inventors: Richard I. Senderoff, Edmonds, WA (US); Shan Jiang, Sammamish, WA (US)

(73) Assignee: Zymogenetics, Inc., Princeton, NJ (US)

( * ) Notice: Subject to any disclaimer, the term of this patent is extended or adjusted under 35 U.S.C. 154(b) by 643 days.

(21) Appl. No.: 12/138,922

(22) Filed: Jun. 13, 2008

(65) Prior Publication Data
US 2008/0311104 A1    Dec. 18, 2008

Related U.S. Application Data

(60) Provisional application No. 60/944,224, filed on Jun. 15, 2007.

(51) Int. Cl.
*A61K 38/43* (2006.01)
(52) U.S. Cl. .................................................. 424/94.64
(58) Field of Classification Search ................ 424/94.64
See application file for complete search history.

(56) References Cited

U.S. PATENT DOCUMENTS

| | | | |
|---|---|---|---|
| 3,879,369 A | 4/1975 | Nolan | |
| 4,696,812 A | 9/1987 | Silbering et al. | |
| 5,130,244 A | 7/1992 | Nishimaki et al. | |
| 5,707,996 A * | 1/1998 | Parrinello | 514/256 |
| 2004/0071769 A1 * | 4/2004 | Farng et al. | 424/450 |
| 2006/0002918 A1 | 1/2006 | Jiang et al. | |
| 2006/0270015 A1 * | 11/2006 | Pawlak et al. | 435/214 |

FOREIGN PATENT DOCUMENTS

| | | |
|---|---|---|
| EP | 1475098 A1 | 11/2004 |
| WO | WO 2006/009989 A1 | 1/2006 |

OTHER PUBLICATIONS

International Search Report mailed Jan. 15, 2009, PCT/US2008/066850.
Gupta & Kaisheva, "Development of a multidose formulation for a humanized monoclonal antibody using experimental design techniques," AAPS Pharm Sci 5(2):E8 (2003).
Maa and Hsu, "Aggregation of recombinant human growth hormone induced by phenolic compounds" Int. J. Pharm. 140:155-168 (1996).
Lam et al., "The Effect of Benzyl Alcohol on Recombinant Human Interferon-upsilon," Pharm. Res. 14:725-729 (1997).

* cited by examiner

*Primary Examiner* — Taeyoon Kim
(74) *Attorney, Agent, or Firm* — Nixon Peabody, LLP; Mary S. Webster

(57) ABSTRACT

Stabilized thrombin compositions, processes for preparing them, and kits comprising them are disclosed. The compositions comprise thrombin, a bacteriostatically effective amount of benzyl alcohol or chlorobutanol, and 0.10%-5.0% (w/v) sucrose in aqueous solution. The compositions are stable when stored at 2° C.-8° C. for four weeks or more.

41 Claims, No Drawings

US 8,071,090 B2

STABILIZED THROMBIN COMPOSITIONS

CROSS-REFERENCE TO RELATED APPLICATIONS

This application claims the benefit of U.S. Provisional Application Ser. No. 60/944,224, filed Jun. 15, 2007, which is incorporated herein by reference.

BACKGROUND OF THE INVENTION

Formulation of pharmaceutical proteins presents significant challenges. Proteins possess multiple functional groups in addition to three-dimensional structure; degradation therefore proceeds via both chemical (modifications involving bond formation or cleavage) and physical (denaturation, aggregation, adsorption, precipitation) pathways. Since each protein embodies a unique combination of amino acid sequence, isoelectric point, and other determinants, its response to changes in solution conditions is unpredictable, and must be determined on a case-by-case basis. Attempts to prevent one form of degradation often increase the rate of another.

Degradation of proteins can be greatly reduced or avoided by lyophilization. However, lyophilization is time consuming and costly, and can cause protein denaturation and aggregation if appropriate excipients are not included. As with solution formulation, stabilization of lyophilized proteins must be dealt with on an individual basis. Sodium chloride can be used to maintain stability during purification and storage by reducing aggregation and precipitation. However, sodium chloride is a problematic excipient in lyophilized formulations because it lowers glass transition temperature, thereby necessitating low primary temperatures and long cycle times. Jiang et al, US 20060002918 A1 disclose methods for stabilizing lyophilized thrombin preparations by formulating the thrombin with sucrose, mannitol, sodium chloride, and a surfactant or high molecular weight polyethylene glycol. However, stabilization of a protein in the lyophilized state does not ensure stability upon reconstitution, and protein solutions must often be discarded if not used promptly after reconstitution. In addition, the in-use handling of a lyophilized drug product is often limited by sterility considerations because the container-closure integrity is compromised during reconstitution. As such, the in-use handling time could be extended if a drug product formulation was stable in the presence of a preservative.

In view of the often high cost of protein therapeutics, means of enhancing the stability of these proteins in solution are needed. In the case of thrombin, various excipients have been proposed for stabilizing the protein. For example, Silbering et al., U.S. Pat. No. 4,696,812 disclose the use of low levels of saline and glycerol to reduce denaturation of thrombin in solution. Nishimaki et al., U.S. Pat. No. 5,130,244 disclose an aqueous thrombin solution containing a sugar and an amino acid as stabilizers.

Despite these advances, there remains a need in the art for preparations of thrombin that can be stored for extended periods of time in liquid form.

SUMMARY OF THE INVENTION

The present invention provides storage-stable compositions of thrombin and related processes and kits. Thrombins for use within the invention include, without limitation, human thrombin, recombinant human thrombin, and bovine thrombin.

Within one aspect of the invention there is provided a pharmaceutical composition comprising thrombin, a bacteriostatically effective amount of a preservative selected from the group consisting of benzyl alcohol and chlorobutanol, and 0.10% to 5.0% (w/v) sucrose in aqueous solution. Within certain embodiments, the composition further comprises one or more of a buffer, a salt, a polyol, a surfactant, an amino acid, or an additional carbohydrate. Within another embodiment, the preservative is benzyl alcohol. Within a related embodiment, the preservative is benzyl alcohol at a concentration of 0.8%-1.5%, v/v. Within another embodiment, the composition further comprises mannitol. Within a related embodiment, mannitol and sucrose are present in the composition at a ratio of mannitol:sucrose greater than 1:1 but not greater than 2.5:1 (w/w).

Within a second aspect of the invention there is provided a composition comprising thrombin, a pharmaceutically acceptable buffer, 0.10% to 5% (w/v) sucrose, and a preservative selected from the group consisting of benzyl alcohol at a concentration of 0.8% to 1.5% (v/v) or chlorobutanol at a concentration of 0.4% to 0.6% (w/v), in aqueous solution at pH 5.7-7.4. Within one embodiment, the preservative is benzyl alcohol. Within a related embodiment, the preservative is benzyl alcohol at a concentration of 0.8%-1.0%, v/v. Within other embodiments the sucrose concentration is 0.5% to 3.0% (w/v) or about 1% (w/v). Within other embodiments the buffer is selected from the group consisting of histidine, citrate, phosphate, Tris, succinate, and acetate buffers. Within another embodiment, the composition further comprises mannitol. Within a related embodiment, mannitol and sucrose are present in the composition at a ratio of mannitol:sucrose greater than 1:1 but not greater than 2.5:1 (w/w). Within another embodiment, the diluent comprises sodium chloride. Within further embodiments, the thrombin is present at a concentration of 0.1 mg/mL to 5.0 mg/mL or a concentration of 0.3 mg/mL to 3.0 mg/mL.

Within a third aspect of the invention there is provided an aqueous composition consisting essentially of 0.03 mg/mL to 1.6 mg/mL thrombin, 0.17% to 1.3% (w/v) sucrose, 1.1% to 1.6% (w/v) mannitol, 0.8% to 2.0% (w/v) NaCl, 0-1.6 mM $CaCl_2$, 0.001% to 0.32% (w/v) of a surfactant or high-molecular-weight polyethylene glycol, a pharmaceutically acceptable buffer, and a bacteriostatically effective amount of a preservative selected from the group consisting of benzyl alcohol and chlorobutanol in aqueous solution at pH 5.7-7.4. The concentration of the buffer is selected to provide approximately physiological pH upon application of the composition in a surgical setting, and the ratio of mannitol:sucrose is greater than 1:1 but not greater than 2.5:1 (w/w). Within one embodiment the ratio of mannitol to sucrose is 1.33:1 (w/w). Within other embodiments the molar ratio of sucrose:thrombin is at least 700:1 or at least 2000:1. Within another embodiment the preservative is benzyl alcohol at a concentration of 0.8% to 1.5% (v/v).

Within a fourth aspect of the invention there is provided a process for preparing a stabilized thrombin solution comprising the steps of (a) providing a lyophilized composition comprising thrombin and a quantity of sucrose sufficient to stabilize the protein in the presence of a bacteriostatically effective amount of a preservative selected from the group consisting of benzyl alcohol and chlorobutanol, (b) providing a diluent comprising a bacteriostatically effective amount of benzyl alcohol or chlorobutanol in water, and (c) combining the lyophilized composition and the diluent to form a solution, wherein the concentration of sucrose in the solution is from 0.10% to 5.0% (w/v). Within certain embodiments the lyophilized composition further comprises a buffer, a salt, or a polyol.

Within a fifth aspect of the invention there is provided a process for preparing a stabilized thrombin solution comprising the steps of (a) providing a lyophilized composition comprising thrombin and at least one pharmaceutically acceptable excipient, and (b) reconstituting the lyophilized composition in a diluent to provide a pharmaceutically acceptable thrombin solution, wherein the diluent is selected to provide in the solution a benzyl alcohol concentration of 0.8% to 1.5% (v/v) and a sucrose concentration of 0.10% to 5% (w/v). Within one embodiment, the solution further comprises mannitol. Within a related embodiment, the solution comprises mannitol and the mannitol and sucrose are present in the solution at a ratio of mannitol:sucrose greater than 1:1 but not greater than 2.5:1 (w/w).

Within a sixth aspect of the invention there is provided a kit comprising (a) a pharmaceutically acceptable diluent comprising a bacteriostatically effective amount of benzyl alcohol or chlorobutanol in water in a first sealed container, and (b) a lyophilized composition comprising thrombin and a quantity of sucrose in a second sealed container, wherein the quantity of sucrose is selected to provide a sucrose concentration of 0.10% to 5.0% (w/v) upon reconstitution of the lyophilized composition with the diluent. Within one embodiment the diluent further comprises NaCl. Within a related embodiment the diluent is bacteriostatic saline. Within another embodiment, the kit further comprises means for transferring the diluent from the first sealed container to the second sealed container. Within further embodiments, the kit comprises an instruction sheet and/or an applicator device, such as a syringe or sprayer. Within an additional embodiment, the first and second sealed containers are packaged in a third container.

Within a seventh aspect of the invention there is provided a process of administering thrombin to a mammal in need thereof, comprising the steps of (a) providing a pharmaceutically acceptable diluent comprising a bacteriostatically effective amount of a preservative selected from the group consisting of benzyl alcohol and chlorobutanol, (b) providing a lyophilized composition comprising thrombin and an amount of sucrose, (c) reconstituting the lyophilized composition with the diluent to form a solution, and (d) delivering the solution to the mammal, wherein the amount of sucrose is selected to provide a sucrose concentration of 0.10% to 5.0% (w/v) upon reconstitution of the lyophilized composition with the diluent. Within one embodiment the diluent is bacteriostatic saline.

These and other aspects of the invention will become evident upon reference to the following description of the invention.

DESCRIPTION OF THE INVENTION

"Bacteriostatic saline" is 0.9% sodium chloride in water (normal saline) containing 0.9% benzyl alcohol as a preservative.

A "bacteriostatically effective amount of a preservative" is an amount that provides a bacteriostatic effect according to the criteria of USP 51, that is an amount sufficient to protect a dosage form of a therapeutic agent from microbiological growth or from microorganisms that are inadvertently introduced during or subsequent to manufacturing. A typical bacteriostatic range for benzyl alcohol is 0.9%-2.0% (v/v), although amounts up to 5% may be used in certain applications. A typical bacteriostatic range for chlorobutanol is 0.4% to 0.6% (w/v). Those skilled in the art will recognize that the required concentration of a preservative will vary somewhat with the composition of the solution; common pharmaceutical excipients may increase or decrease bacteriostatic activity. The actual concentration required for any solution can be determined according to standard testing procedures.

As used herein, a "diluent" is a solution that dilutes or renders less potent a therapeutic agent. The term is used to include such solutions that are used to reconstitute dried (e.g., lyophilized) therapeutic agents. A "pharmaceutically acceptable diluent" is a diluent that is on the GRAS (generally recognized as safe) list as recognized by pharmaceutical regulatory bodies. Commonly used pharmaceutically acceptable diluents include sterile water USP, normal saline USP, and 5% dextrose USP.

As used herein, "thrombin" denotes the activated enzyme, also known as □-thrombin, which results from the proteolytic cleavage of prothrombin (factor II). As disclosed below, thrombin can be prepared by a variety of methods known in the art, and the term "thrombin" is not intended to imply a particular method of production. Human thrombin is a 295 amino acid protein composed of two polypeptide chains joined by a disulfide bond. Both human and non-human (e.g., bovine) thrombins can be used within the present invention. Thrombin is used medically as a hemostatic agent and as a component of tissue adhesives.

Human and non-human thrombins are prepared according to methods known in the art. Purification of thrombin from plasma is disclosed by, for example, Bui-Khac et al., U.S. Pat. No. 5,981,254. Purification of thrombin from plasma fractions, such as Cohn fraction III, is disclosed by Fenton et al., *J. Biol Chem.* 252:3587-3598, 1977. Recombinant thrombin can be prepared from a prethrombin precursor by activation with a snake venom activator as disclosed in U.S. Pat. No. 5,476,777. Suitable venom activators include ecarin and prothrombin activator from *Oxyuranus scutellatus*. Other activators, such as factor Xa, can also be employed.

Highly purified thrombin has a specific activity of approximately 3200 NIH Units per mg or 3800 International Units per mg. One NIH Unit equals 1.19 International Unit. The abbreviation "U" is used herein to denote "Units" and indicates NIH units unless specified otherwise. The abbreviation "IU" is used to denote International Units.

Numerical ranges (e.g., "from X to Y") include the endpoints unless otherwise specified.

The terms "about" and "approximately" denote a range of error of ±10% of the stated value. For example, "about 1%" is used to denote a range of 0.9% to 1.1%, inclusive.

All references cited herein are incorporated by reference in their entirety.

The present invention provides methods for stabilizing thrombin in solution. The inventors have found that a previously disclosed (Jiang et al., US 20060002918 A1) lyophilized formulation of recombinant human thrombin, when reconstituted with bacteriostatic saline, remains stable at refrigerator temperature for up to thirteen weeks. This result was unexpected in view of the known tendency of preservatives such as benzyl alcohol to denature proteins and increase aggregation rates (e.g., Gupta and Kaisheva, *AAPS Pharm Sci* 5(2):E8, 2003; Maa and Hsu, *Int. J. Pharm.* 140:155-168, 1996; Lam et al., *Pharm. Res.* 14:725-729, 1997). When a preparation of bovine thrombin (THROMBIN-JMI, King Pharmaceuticals, Inc.) was reconstituted with bacteriostatic saline, the solution became hazy. It was discovered that the haziness of the latter preparation could be avoided by adding sucrose to the diluent used to reconstitute it.

Compositions of the present invention comprise, in aqueous solution, thrombin, a bacteriostatically effective amount of a preservative selected from the group consisting of benzyl alcohol and chlorobutanol, and sucrose to stabilize the thrombin against degradation induced by the preservative. The concentration of sucrose in the composition is from 0.10% to 5.0% (w/v), often 0.17% to 5.0%, usually 0.17% to 3.0%, more commonly 0.5% to 2.0%. Within certain embodiments of the invention the concentration of sucrose is 1% (w/v). The thrombin compositions are stable at refrigerator temperatures for at least four weeks. Recombinant human thrombin solutions of this type have been found to remain stable when tested after six and thirteen weeks of storage at 2° C.-8° C.

As will be evident to those skilled in the art, the compositions may comprise additional components, such as buffers, bulking agents, lyoprotectants, solubilizers, surfactants, carbohydrates, polyols, amino acids, additional carbohydrates (e.g., trehalose), and/or tonicity adjusting agents (e.g., salts, mannitol). Selection of actual components is a matter of routine design choice and is within the level of ordinary skill in the art. See for example, Remington: the Science and Practice of Pharmacy, 21st ed., Lippincott Williams & Wilkins, Baltimore, 2005.

Thrombin is commonly provided as a lyophilized powder or cake that can be reconstituted by adding a pharmaceutically acceptable diluent and mixing. The diluent will ordinarily contain the preservative (e.g., benzyl alcohol or chlorobutanol). The diluent volume is selected to provide a solution having a final sucrose concentration of 0.10% to 5.0% (w/v). Sucrose may be present in the lyophilized thrombin formulation, the diluent, or both, so long as the total concentration of sucrose in the reconstituted solution is within the range of 0.10% to 5.0%, 0.17% to 5.0%, 0.17% to 3.0%, or 0.5% to 2.0% (w/v). The lyophilized formulation may also contain a buffer as disclosed in more detail below. In one embodiment, the formulation contains mannitol as a bulking agent. In preferred formulations, mannitol is included at a ratio of mannitol:sucrose greater than 1:1 but not greater than 2.5:1 (w/w). The actual selection of the diluent will be made in view of the composition of the lyophilized formulation and the intended use of the product. However, the invention is not limited by the manner in which the composition is made or the order in which its constituents are combined. For example, a lyophilized formulation of thrombin containing one or more lyoprotectants can be reconstituted with a pharmaceutically acceptable diluent containing the preservative and sucrose, and optionally containing additional components as disclosed above. If long term storage is not required or stability is augmented by storage at temperatures below freezing (<0° C.), purified thrombin can be formulated with the preservative, the sucrose, and optionally other components, without preparing a lyophilized formulation.

Any pharmaceutically acceptable buffer may be employed within the present invention. It is preferred to select a buffer that provides a slightly acidic to approximately neutral pH to limit loss of thrombin activity due to autolysis (formation of inactive autolytic degradation products including β- and γ-thrombin), which increases above pH 6.0, and precipitation, which increases below pH 6.0. It is therefore advantageous to use a weak buffer that is effective at slightly acidic to approximately neutral pH (i.e, pH 5.7-7.4), but will allow the pH to reach physiological pH (i.e. pH 7.35-7.45) when the thrombin is applied to bleeding tissue, thereby providing optimal biological activity. Thrombin compositions buffered to a pH of 6.0-6.5 are preferred. Examples of suitable buffers include histidine, phosphate, citrate, Tris (2-Amino-2-(hydroxymethyl)-1,3-propanediol), and succinate buffers. For example, histidine buffer can be included at a concentration of 1-20 mM, usually 2-10 mM, and more often about 5 mM.

Suitable concentrations of other buffers for use within the present invention can be readily determined by one of ordinary skill in the art. Formulation buffers can be tested by adding blood and measuring the pH of the resulting solution. In an exemplary assay, aliquots of rabbit blood are added stepwise to various buffers, and pH is measured after each addition. When histidine buffers are tested in such an assay, 3.2 mM, 5 mM, 12.8 mM, and 20 mM histidine are neutralized by the addition of not more than 1.0 volume of blood. In contrast, 160 mM succinate buffer and 90 mM phosphate/12.8 mM histidine buffer did not produce a mixture with a pH above 7.0 even after addition of 2-3 volumes of blood. Thus, when buffers such as succinate or phosphate/histidine are used, lower concentrations are preferred.

Typical thrombin compositions within the present invention consist essentially of 0.03 mg/mL to 1.6 mg/mL thrombin, 0.17% to 1.3% (w/v) sucrose, a bacteriostatically effective amount of benzyl alcohol or chlorobutanol, 1.1% to 1.6% (w/v) mannitol, 0.8% to 2.0% (w/v) NaCl, 0-1.6 mM $CaCl_2$, 0.001% to 0.32% (w/v) of a surfactant (e.g., polyethylene oxides, sorbitan esters, polyoxyethylene alkyl ethers, glycerides of fatty acids, or polyoxyethylene sorbitan fatty acid esters) or high-molecular-weight polyethylene glycol (e.g., PEG 400, PEG 1000, PEG 3350, PEG 5000, or PEG 8000), and a pharmaceutically acceptable buffer at pH 5.7-7.4. In certain preferred compositions, the ratio of mannitol:sucrose is greater than 1:1 but not greater than 2.5:1 (w/w).

The concentration of thrombin within the compositions of the present invention can be varied, depending on the intended use, by adjusting the dilution volume. For topical application to control bleeding, the thrombin concentration will generally be from about 100 U/mL to about 20,000 U/mL (approximately 0.026 mg □-thrombin per mL to 5.26 mg □-thrombin per mL), more commonly about 300 U/mL to about 5,000 U/mL, typically about 1,000 U/mL, although the actual concentration will be determined by the physician according to the needs of the individual patient. The thrombin solution can be used immediately, held at room temperature for up to 48 hours, or stored under refrigeration for up to four weeks or more. The thrombin can be applied to bleeding tissue to achieve hemostasis, often in combination with an absorbable gelatin sponge or other delivery vehicle according to conventional surgical practice. The thrombin can also be used as a component of a tissue adhesive or fibrin glue. These and other uses of thrombin are known in the art.

The invention further provides thrombin in a kit comprising a diluent in a first sealed container and lyophilized thrombin in a second sealed container. The diluent comprises a bacteriostatically effective amount of benzyl alcohol or chlorobutanol. In typical embodiments the diluent is normal saline (0.9% w/v sodium chloride solution) containing the benzyl alcohol or chlorobutanol. The kit may further comprise an application device, such as a sprayer, syringe, or the like, as well as one or more needles or other transfer devices to facilitate transfer of liquid into and out of the containers. A variety of such devices, including needleless transfer devices, are known in the art. See, for example, U.S. Pat. No. 6,558,365. An instruction sheet may also be packaged in the kit. Commonly, the first and second sealed containers will be packaged in a third container. The contents of the kit will ordinarily be sterile. The third container may also be sterile.

The invention is further illustrated by the following non-limiting examples.

EXAMPLES

Example 1

Recombinant human thrombin (rhThrombin) was formulated at 1 mg/mL (3200 U/mL) in 5 mM histidine, 150 mM NaCl, 4 mM $CaCl_2$, 0.1% PEG3350, pH 6.0 with varying concentrations of mannitol and sucrose as shown in Table 1.

TABLE 1

| Formulation | Mannitol | Sucrose |
| --- | --- | --- |
| T | 5% | 0.5% |
| A | 5% | 1% |
| B | 5% | 2% |
| C | 5% | 3% |
| D | 4% | 3% |
| E | 3% | 3% |
| F | — | 5% |

1.6-mL aliquots of the solutions were placed in vials and lyophilized under the conditions shown in Table 2. For subsequent analysis, lyophilized samples were reconstituted with water where necessary. Visual observations of lyophilized and reconstituted samples are shown in Table 3.

TABLE 2

| Formulation | Freezing & Annealing | Primary Drying | Secondary Drying |
| --- | --- | --- | --- |
| T | 0.5° C./min to 5° C., hold 0.5 hr<br>0.25° C./min to −50° C., hold 2 hr<br>0.25° C./min to −30° C., hold 3 hr<br>0.25° C./min to −50° C., hold 2 hr | 0.5° C./min to −10° C., hold 16 hr<br>60 mTorr | 0.2° C./min to 30° C., hold 24 hr<br>60 mTorr |
| A, B, C, D, E, F | 0.5° C./min to 5° C., hold 2 hr<br>0.5° C./min to −50° C., hold 2 hr<br>0.25° C./min to −20° C., hold 2 hr<br>0.25° C./min to −25° C., hold 2 hr<br>0.25° C./min to −50° C., hold 2 hr | 0.5° C./min to −30° C., hold 10 hr<br>0.5° C./min to −25° C., hold 10 hr<br>0.5° C./min to −20° C., hold 10 hr<br>0.5° C./min to −15° C., hold 10 hr<br>60 mTorr | 0.5° C./min to 25° C., hold 24 hr<br>0.5° C./min to 30° C., hold 8 hr<br>0.5° C./min to 20° C., hold 6 hr<br>60 mTorr |

TABLE 3

| Formulation | Lyophilized Solid | Reconstituted Solution |
| --- | --- | --- |
| T | White cake | Clear |
| A | White cake | Clear |
| B | White cake | Clear |
| C | White cake | Clear |
| D | White cake | Clear |
| E | White semi-collapsed cake or white powder | Clear |
| F | White powder | Clear |

Example 2

Recombinant human thrombin was formulated at 1 mg/mL in 5 mM histidine, 3% (w/v) sucrose, 4% (w/v) mannitol, 150 mM NaCl, 4 mM $CaCl_2$, 0.1% PEG3350, pH 6.0. 1.6-mL aliquots of the solution were placed in vials and lyophilized under the conditions shown in Table 4.

TABLE 4

| Freezing & Annealing | Primary Drying | Secondary Drying |
| --- | --- | --- |
| 0.5° C./min to 5° C., hold 2 hr<br>0.25° C./min to −52° C., hold 4 hr<br>0.5° C./min to −25° C., hold 2 hr<br>0.5° C./min to −52° C., hold 4 hr | 0.5° C./min to −10° C., hold 26 hr; 60 mTorr | 0.5° C./min to 30° C., hold 24 hr; 60 mTorr |

Example 3

One vial (5,000 IU) each of recombinant human thrombin ("rhThrombin DP," prepared as disclosed in Example 2) and bovine thrombin (THROMBIN-JMI, Jones Pharma Incorporated, Bristol, Va.; lyophilized powder containing mannitol and sodium chloride) were reconstituted with 5 mL of bacteriostatic saline USP. The bovine thrombin appeared colorless, hazy and frothy upon reconstitution, while the recombinant thrombin was colorless and clear. Following storage at 25° C. for 48 hours, the bovine thrombin was colorless with a visible precipitate, and the recombinant thrombin remained colorless and clear.

Example 4

One vial (5,000 IU) each of rhThrombin DP, recombinant human thrombin pilot formulation (Example 1, formulation T), and bovine thrombin (THROMBIN-JMI) were reconstituted with 5.0 mL of bacteriostatic saline USP. Sucrose concentrations in the reconstituted solutions were 0% in the bovine thrombin, 0.17% in the pilot thrombin, and 1.0% in the rhThrombin DP. Both of the rhThrombin solutions were clear, while the bovine thrombin solution appeared hazy.

Example 5

Vials of rhThrombin DP (5,000 IU) were reconstituted with 5 mL bacteriostatic saline injection, USP (n=3). The reconstituted samples were stored inverted at 2-8° C. for 1, 2, 4, 6, 9, and 13 weeks, and at 25° C. for 8, 24, and 48 hours. After storage, the samples were analyzed for appearance, content (by RP-HPLC), purity (RP-HPLC), potency (clotting activity), and high-molecular-weight (HMW) impurities (SE-HPLC). As shown in Table 5, no remarkable instabilities were observed for the time periods and conditions that were evaluated.

TABLE 5

| Time Point | Content (mg/mL) | Purity (%) | HMW (%) | Clotting Activity (IU/mL) | Specific Activity (IU/mg) |
|---|---|---|---|---|---|
| 25° C. (n = 3) | | | | | |
| Initial | 0.34 | 91.3 | <0.2 | 1254 | 3724 |
| 8 hr | 0.33 | 91.7 | <0.2 | 1261 | 3784 |
| 24 hr | 0.33 | 92.1 | <0.2 | 1245 | 3735 |
| 48 hr | 0.33 | 92.5 | <0.2 | 1226 | 3679 |
| 2-8° C. (n = 3) | | | | | |
| 1 week | 0.33 | 91.9 | <0.2 | 1170 | 3582 |
| 2 week | 0.32 | 91.8 | <0.2 | 1164 | 3601 |
| 4 week | 0.33 | 91.7 | <0.2 | 1182 | 3546 |
| 6 week | 0.33 | 92.2 | <0.2 | 1243 | 3766 |
| 9 week | 0.33 | 92.1 | <0.2 | 1136 | 3479 |
| 13 week | 0.32 | 91.9 | <0.2 | 1102 | 3443 |

Example 6

Vials of rhThrombin DP and pilot formulation (5,000 IU each) were reconstituted with 1.6 mL of bacteriostatic saline. Sucrose concentration was 3.0% in the rhThrombin DP solution and 0.5% in the pilot thrombin solution. No precipitation was observed right after reconstitution or after 24 or 48 hours at 25° C.

Example 7

Three vials of recombinant human thrombin DP (5,000 IU) were each reconstituted with 5 mL bacteriostatic saline. No precipitation was observed after 13 weeks of storage at 2-8° C.

Example 8

Recombinant human thrombin DP was reconstituted with 0.9% or 2.0% benzyl alcohol in normal saline. Samples were stored at 25° C. No precipitation was observed in the 0.9% samples immediately after reconstitution or after 48 hours. Samples containing 2.0% benzyl alcohol showed no precipitation immediately after reconstitution, but showed precipitation at 24 hours.

Example 9

Bovine thrombin was reconstituted with bacteriostatic saline containing 1% sucrose. Samples were stored at 25° C. No precipitation was observed immediately after reconstitution or after 24 or 48 hours.

Example 10

The following preservatives were individually added to samples of recombinant human thrombin DP, reconstituted with normal saline: phenol (1%, w/v), m-cresol (0.2%, v/v), methylparaben (0.5%, w/v), propylparaben (1%, w/v), or chlorobutanol (0.5%, w/v). Samples were stored at 25° C. Precipitation was observed in the phenol and m-cresol samples after 24 hours. Samples containing 0.5% chlorobutanol remained clear at 24 and 48 hours. Methylparaben and propylparaben were not soluble in saline at the tested concentrations.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A pharmaceutical composition comprising:
   thrombin;
   a bacteriostatically effective amount of a preservative selected from the group consisting of benzyl alcohol and chlorobutanol; and 0.10% to 5.0% (w/v) sucrose in aqueous solution.

2. The composition of claim 1 further comprising one or more of a buffer, a salt, a polyol, a surfactant, an amino acid, or an additional carbohydrate.

3. The composition of claim 1 wherein the preservative is benzyl alcohol.

4. The composition of claim 3 wherein the benzyl alcohol is present at a concentration of 0.8%-1.5% (v/v).

5. The composition of claim 1, further comprising mannitol.

6. The composition of claim 5 wherein the mannitol and sucrose are present at a ratio of mannitol:sucrose greater than 1:1 but not greater than 2.5:1 (w/w).

7. The composition of claim 1 wherein the thrombin is human thrombin.

8. The composition of claim 7 wherein the human thrombin is recombinant human thrombin.

9. The composition of claim 1 wherein the thrombin is bovine thrombin.

10. A composition comprising:
    thrombin;
    a pharmaceutically acceptable buffer; 0.10% to 5% (w/v) sucrose; and a preservative selected from the group consisting of benzyl alcohol at a concentration of 0.8% to 1.5% (v/v) or chlorobutanol at a concentration of 0.4% to 0.6% (w/v), in aqueous solution at pH 5.7-7.4.

11. The composition of claim 10 wherein the preservative is benzyl alcohol.

12. The composition of claim 11 wherein the concentration of benzyl alcohol is 0.8% to 1.0% (v/v).

13. The composition of claim 10 wherein the sucrose concentration is 0.5% to 3.0% (w/v).

14. The composition of claim 10 wherein the sucrose concentration is about 1% (w/v).

15. The composition of claim 10 wherein the buffer is selected from the group consisting of histidine, citrate, phosphate, Tris, succinate, and acetate buffers.

16. The composition of claim 10, further comprising mannitol.

17. The composition of claim 16 wherein the mannitol and sucrose are present at a ratio of mannitol:sucrose greater than 1:1 but not greater than 2.5:1 (w/w).

18. The composition of claim 10 wherein the diluent comprises sodium chloride.

19. The composition of claim 10 wherein the thrombin is human thrombin.

20. The composition of claim 19 wherein the human thrombin is recombinant human thrombin.

21. The composition of claim 10 wherein the thrombin is bovine thrombin.

22. The composition of claim 10 wherein the thrombin is present at a concentration of 0.1 mg/mL to 5.0 mg/mL.

23. The composition of claim 22 wherein the thrombin is present at a concentration of 0.3 mg/mL to 3.0 mg/mL.

24. An aqueous composition consisting essentially of:
0.03 mg/mL to 1.6 mg/mL thrombin;
0.17% to 1.3% (w/v) sucrose;
1.1% to 1.6% (w/v) mannitol;
0.8% to 2.0% (w/v) NaCl;
0-1.6 mM $CaCl_2$;
0.001% to 0.32% (w/v) of a surfactant or high-molecular-weight polyethylene glycol;
a pharmaceutically acceptable buffer; and
a bacteriostatically effective amount of a preservative selected from the group consisting of benzyl alcohol and chlorobutanol, in aqueous solution at pH 5.7-7.4,
wherein concentration of the buffer is selected to provide approximately physiological pH upon application of the composition in a surgical setting and wherein the ratio of mannitol:sucrose is greater than 1:1 but not greater than 2.5:1 (w/w).

25. The composition of claim 24 wherein the ratio of mannitol to sucrose is 1.33:1 (w/w).

26. The composition of claim 24 wherein the molar ratio of sucrose:thrombin is at least 700:1.

27. The composition of claim 26 wherein the molar ratio of sucrose:thrombin is at least 2000:1.

28. The composition of claim 24 wherein the preservative is benzyl alcohol at a concentration of 0.8% to 1.5% (v/v).

29. A process for preparing a stabilized thrombin solution comprising:
providing a lyophilized composition comprising thrombin and a quantity of sucrose sufficient to stabilize the protein in the presence of a bacteriostatically effective amount of a preservative selected from the group consisting of benzyl alcohol and chlorobutanol; providing a diluent comprising a bacteriostatically effective amount of benzyl alcohol or chlorobutanol in water; and
combining the lyophilized composition and the diluent to form a solution, wherein the concentration of sucrose in the solution is from 0.10% to 5.0% (w/v).

30. The process of claim 29 wherein the lyophilized composition further comprises a buffer, a salt, or a polyol.

31. A process for preparing a stabilized thrombin solution comprising:
providing a lyophilized composition comprising thrombin and at least one pharmaceutically acceptable excipient; and reconstituting the lyophilized composition in a diluent to provide a pharmaceutically acceptable thrombin solution, wherein the diluent is selected to provide in the solution a benzyl alcohol concentration of 0.8% to 1.5% (v/v) and a sucrose concentration of 0.10% to 5% (w/v).

32. The process of claim 31 wherein the solution further comprises mannitol.

33. The process of claim 32 wherein the mannitol and sucrose are present in the solution at a ratio of mannitol:sucrose greater than 1:1 but not greater than 2.5:1 (w/w).

34. A kit comprising:
a pharmaceutically acceptable diluent comprising a bacteriostatically effective amount of benzyl alcohol or chlorobutanol in water in a first sealed container; and
a lyophilized composition comprising thrombin and a quantity of sucrose in a second sealed container, wherein the quantity of sucrose is selected to provide a sucrose concentration of 0.10% to 5.0% (w/v) upon reconstitution of the lyophilized composition with the diluent.

35. The kit of claim 34 wherein the diluent further comprises NaCl.

36. The kit of claim 35 wherein the diluent is bacteriostatic saline.

37. The kit of claim 34, further comprising means for transferring the diluent from the first sealed container to the second sealed container.

38. The kit of claim 34, further comprising an instruction sheet.

39. The kit of claim 34, further comprising an applicator device.

40. The kit of claim 39, wherein the applicator device is a syringe or a sprayer.

41. The kit of claim 34, wherein the first and second sealed containers are packaged in a third container.

* * * * *